US009198647B2

(12) United States Patent
Kleyman

(10) Patent No.: US 9,198,647 B2
(45) Date of Patent: Dec. 1, 2015

(54) FLEXIBLE ACCESS ASSEMBLY

(71) Applicant: Covidien LP, Mansfield, MA (US)

(72) Inventor: Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 73 days.

(21) Appl. No.: 14/164,305

(22) Filed: Jan. 27, 2014

(65) Prior Publication Data

US 2014/0243601 A1    Aug. 28, 2014

Related U.S. Application Data

(60) Provisional application No. 61/768,568, filed on Feb. 25, 2013.

(51) Int. Cl.
| | |
|---|---|
| *A61B 1/32* | (2006.01) |
| *A61B 17/02* | (2006.01) |
| *A61B 17/34* | (2006.01) |
| *A61B 17/00* | (2006.01) |

(52) U.S. Cl.
CPC ......... *A61B 17/0218* (2013.01); *A61B 17/3417* (2013.01); *A61B 17/3421* (2013.01); *A61B 17/3423* (2013.01); *A61B 2017/00738* (2013.01); *A61B 2017/3466* (2013.01)

(58) Field of Classification Search
CPC ........... A61B 17/0218; A61B 17/3417; A61B 17/3421; A61B 17/3423; A61B 2017/00738; A61B 2017/3466
USPC ........ 600/204; 604/104, 264, 164.01, 164.06, 604/164.11, 164.12, 170.02, 170.03
See application file for complete search history.

(56) References Cited

U.S. PATENT DOCUMENTS

| | | | |
|---|---|---|---|
| 4,682,978 A | | 7/1987 | Martin |
| 4,756,708 A | * | 7/1988 | Martin ..................... 604/170.03 |
| 4,863,430 A | | 9/1989 | Klyce et al. |
| 5,749,859 A | | 5/1998 | Powell |
| 6,689,152 B2 | | 2/2004 | Balceta et al. |
| 6,761,718 B2 | | 7/2004 | Madsen |

(Continued)

FOREIGN PATENT DOCUMENTS

| | | |
|---|---|---|
| WO | 2004/016184 A1 | 2/2004 |
| WO | 2006/100658 A2 | 9/2006 |

OTHER PUBLICATIONS

European Search Report from corresponding EP 14156341.1 dated Apr. 15, 2014.

*Primary Examiner* — Pedro Philogene
*Assistant Examiner* — David C Comstock

(57) ABSTRACT

A cannula assembly includes a cannula and an obturator. The cannula includes an elongated shaft dimensioned to access tissue. The elongated shaft has a lumen extending therethrough. The elongated shaft includes a first shaft segment having a first pre-determined configuration and a second shaft segment having a second pre-determined configuration different from the first pre-determined configuration. The obturator includes an elongated body adapted for insertion through the lumen of the elongated shaft. The elongated body includes a first body segment having a configuration in general accordance with the first pre-determined configuration of the first shaft segment and a second body segment selectively adaptable to conform to the second pre-determined configuration of the second shaft segment upon insertion through the lumen of the elongated shaft.

17 Claims, 6 Drawing Sheets

(56) References Cited

U.S. PATENT DOCUMENTS

| | | |
|---|---|---|
| 7,344,554 B2 | 3/2008 | Kuyava et al. |
| 2002/0058910 A1 | 5/2002 | Hermann et al. |
| 2002/0173689 A1* | 11/2002 | Kaplan .......................... 600/7 |
| 2003/0130668 A1 | 7/2003 | Nieman et al. |
| 2004/0162559 A1* | 8/2004 | Arramon et al. ............... 606/62 |
| 2004/0210245 A1 | 10/2004 | Erickson et al. |
| 2005/0107816 A1 | 5/2005 | Pingleton et al. |
| 2006/0015006 A1 | 1/2006 | Laurence et al. |
| 2006/0063965 A1 | 3/2006 | Aboul-Hosn et al. |
| 2007/0078478 A1 | 4/2007 | Atkins et al. |
| 2007/0203474 A1 | 8/2007 | Ryan et al. |
| 2009/0082731 A1 | 3/2009 | Moreno |
| 2009/0093752 A1* | 4/2009 | Richard et al. ................. 604/24 |
| 2009/0187079 A1 | 7/2009 | Albrecht et al. |
| 2009/0318870 A1 | 12/2009 | Patterson et al. |
| 2010/0280368 A1 | 11/2010 | Can et al. |

\* cited by examiner

FLEXIBLE ACCESS ASSEMBLY

CROSS-REFERENCE TO RELATED APPLICATIONS

This application claims the benefit of and priority to U.S. Provisional Patent Application No. 61/768,568, filed Feb. 25, 2013, the entire disclosure of which is incorporated by reference herein.

BACKGROUND

1. Technical Field

The present disclosure relates to surgical instruments and, more particularly, to access assemblies for providing access to internal body cavities, tissues and organs.

2. Background of Related Art

Laparoscopic surgical procedures are minimally invasive procedures in which operations are carried out within the body by means of elongated instruments inserted through small incisions in the body. Laparoscopic procedures are desirable in that they improve patient recovery time and minimize hospital stays as compared to open surgical procedures. Laparoscopic procedures also leave minimal scarring (both internally and externally) and reduce patient discomfort during the recovery period.

During a typical laparoscopic, or minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

Due to the relatively small interior dimensions of the cannulas and/or access ports used in laparoscopic procedures, only elongated, small diametered instrumentation may be used to access the internal body cavities and organs. The manipulation of such instruments within the internal body is similarly limited by both spatial constraints and the need to maintain the body cavity in an insufflated state.

SUMMARY

In accordance with the present disclosure, a cannula assembly is provided. The cannula assembly includes a cannula and an obturator. The cannula includes an elongated shaft dimensioned to access tissue. The elongated shaft has a lumen extending therethrough, defines a longitudinal axis and has proximal and distal ends. The elongated shaft further includes a first shaft segment having a first pre-determined configuration and a second shaft segment having a second pre-determined configuration that is different from the first pre-determined configuration. The obturator includes an elongated body adapted for insertion through the lumen of the elongated shaft. The elongated body has proximal and distal ends. The elongated body further includes a first body segment having a configuration in general accordance with the first pre-determined configuration of the first shaft segment and a second body segment selectively adaptable to conform to the second pre-determined configuration of the second shaft segment upon insertion through the lumen of the elongated shaft.

In one embodiment, the first pre-determined configuration of the first shaft segment defines a general linear segment and the first body segment of the elongated body defines a generally corresponding linear segment.

In another embodiment, the second pre-determined configuration of the second shaft segment defines a general arcuate segment. Upon insertion of the elongated body through the lumen of the elongated shaft, the second body portion of the elongated body is positioned in the second pre-determined configuration having a generally corresponding arcuate segment.

In yet another embodiment, the second shaft segment of the elongated shaft is disposed adjacent the distal end of the elongated shaft. Alternatively, the second shaft segment of the elongated shaft may be disposed intermediate the proximal and distal ends of the elongated shaft.

In still another embodiment, the distal end of the elongated body defines a conical-shaped configuration to facilitate advancement through tissue.

In still yet another embodiment, the elongated body of the obturator defines a longitudinal axis. The second body segment of the elongated body is initially positioned in general alignment with the longitudinal axis. However, upon insertion of the elongated body through the lumen of the elongated shaft, the second body segment is positioned in general oblique relation with the longitudinal axis in general accordance with the second pre-determined configuration of the second shaft segment.

A surgical access system is also provided in accordance with the present disclosure. The surgical access system includes an anchor member and a cannula assembly. The anchor member is positionable within a passage in tissue. The anchor member includes a compressible material and defines a proximal end, a distal end and an intermediate portion. The anchor member is adapted to transition between an at least partially compressed condition to facilitate introduction within the passage in tissue and an at least partially expanded condition to substantially anchor the anchor member relative to the tissue. The anchor member further includes one or more ports extending therethrough. The cannula assembly includes a cannula defining a longitudinal axis and a lumen extending therethrough. The cannula includes a cannula segment offset with respect to the longitudinal axis.

The access system may include an obturator having an elongated obturator body adapted for insertion through the lumen of the cannula. The obturator body has a flexible body segment adapted to follow the path defined by the offset cannula segment. The elongated body has an end dimensioned to extend beyond the cannula and configured to facilitate advancement of the obturator and cannula through the one or more ports of the anchor member with the internal surfaces defining the at least one port of the anchor member establishing a substantial seal about the cannula.

In embodiments, the cannula assembly may be configured according to any of the embodiments of the cannula assembly discussed above.

In another embodiment, a surgical instrument having a flexible shaft segment and an end effector adapted to perform a surgical task is dimensioned for advancement through the lumen of the cannula in the absence of the obturator whereby the flexible shaft segment follows the path defined by the offset cannula segment.

BRIEF DESCRIPTION OF THE DRAWINGS

Various embodiments of the subject instrument are described herein with reference to the drawings wherein.

DETAILED DESCRIPTION

Figure 3:
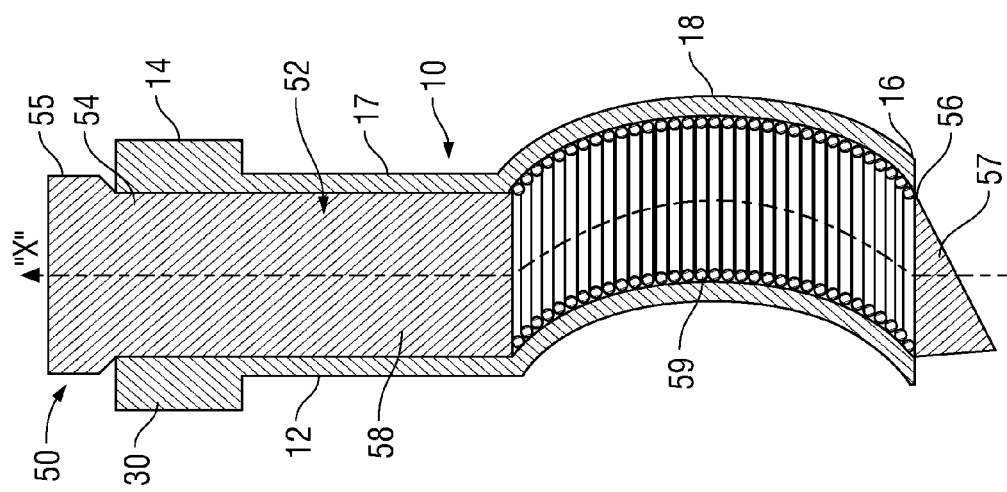
FIG. 3 is a side, cross-sectional view showing the obturator of FIG. 2 inserted through the pre-bent access instrument of FIG. 1.

Embodiments of the presently disclosed surgical instruments will now be described in detail with reference to the drawing figures wherein like reference numerals identify similar or identical structural elements. As shown in the drawings and described throughout the following description, as is traditional when referring to relative positioning on a surgical instrument, the term "proximal" or "trailing" refers to the end of the apparatus which is closer to the user and the term "distal" or "leading" refers to the end of the apparatus which is further away from the user.

Figure 1:
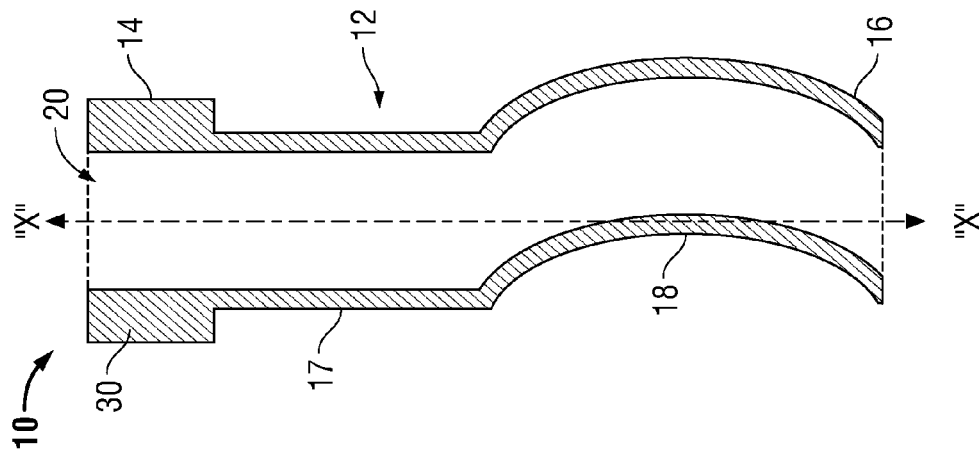
FIG. 1 is a side, cross-sectional view of one embodiment of a pre-bent access instrument in accordance with the present disclosure.

Turning now to FIG. 1, a surgical instrument according to the present disclosure is shown generally indentified by reference numeral 10. Access instrument 10 includes an elongated shaft 12 having a proximal end 14, a distal end 16 and defining a lumen, or passageway 20 therethrough. Access instrument 10 may be configured as an access portal, e.g., a trocar or a cannula, for providing access to internal body cavities and organs. More specifically, surgical instruments, fluids and/or medicaments may be inserted through lumen 20 of access instrument 10 for use at an internal surgical site. Further, a seal member 30 may be disposed at proximal end 14 of shaft 12 for sealingly engaging an instrument (or instruments), e.g., an obturator 50 (see FIG. 2), inserted through lumen 20.

Elongated shaft 12 of access instrument 10 includes a linear portion 17 and an arcuate, or curved portion 18. Linear portion 17 is disposed about longitudinal axis "X," while curved portion 18 bends, curves off, or is obliquely arranged with respect to longitudinal axis "X." Although a specific configuration of curved portion 18 is shown in FIG. 1, it is envisioned that curved portion 18 may define various curved, angled, or other bent configurations. Elongated shaft 12 may be formed from any suitable rigid, or semi-rigid medical grade material, e.g., stainless steel, or other suitable bio-compatible materials, e.g., polymeric materials. It is also envisioned that elongated shaft 12 may be formed at least partially from a shape memory material which undergoes a shape-transformation when subject to body temperatures, thereby shaping the surgical instrument, e.g., access instrument 10, to a desired pre-bent, or curved configuration.

Figure 2:
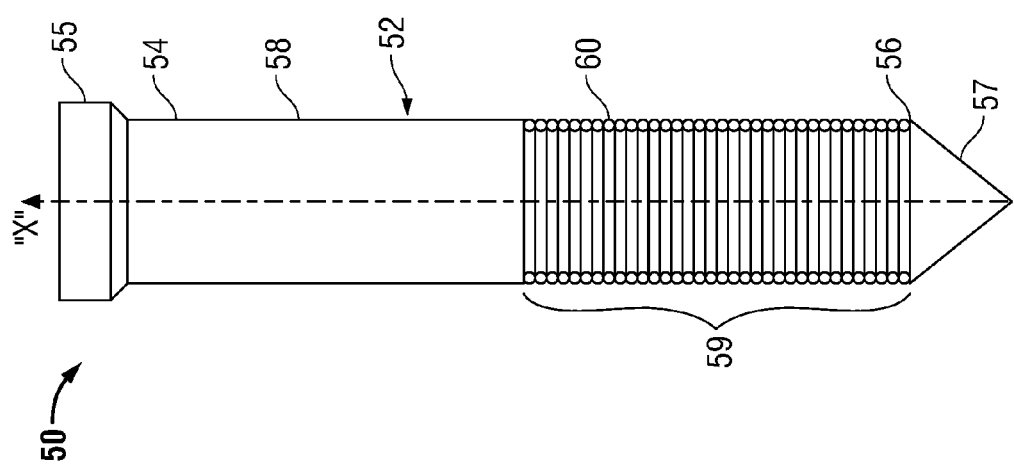
FIG. 2 is a side plan view of a partially-bendable obturator for use with the pre-bent access instrument of FIG. 1.

An obturator 50 for use with access instrument 10 is shown in FIG. 2. Obturator 50 includes a shaft 52 having a proximal end 54 and a distal end 56 and is configured for insertion through lumen 20 of access instrument 10. A hub 55 is disposed at proximal end 54 of shaft 52, while distal end 56 of shaft 52 includes a pointed distal tip 57.

Shaft 52 of obturator 50 includes a relatively rigid portion 58 and a less-rigid, or flexible portion 59. Rigid portion 58 of shaft 52 may be formed from any suitable medical grade material, e.g., stainless steel, or other suitable rigid bio-compatible material, e.g., polymeric materials. As shown in FIG. 2, flexible portion 59 of shaft 52 may be formed from a spring coil 60 or, alternatively, flexible portion 59 of shaft 52 may be formed from bio-compatible flexible tubing (not shown) or any other suitable resiliently flexible material. Further, flexible portion 59 may define a length that is equal to, or greater than a length of curved portion 18 of access instrument 10, such that as, shown in FIG. 3, obturator 50 is positionable within lumen 20 of access instrument 10 to conform to the configuration, or shape of access instrument 10.

With continued reference to FIG. 2, rigid portion 58 of shaft 52 is coaxially disposed about longitudinal axis "X," and provides structural support to shaft 52, while flexible portion 59 is capable of being bent or angulated relative to the longitudinal axis "X" of shaft 52 in any radial direction to conform obturator 50 to a desired configuration, e.g., the pre-bent configuration of shaft 12 of cannula or access instrument 10. However, although flexible portion 59 is radially deflectable, it is envisioned that flexible portion 59 of shaft 52 may be substantially rigid, in the axial direction.

FIG. 3 illustrates obturator 50 inserted through and positioned within lumen 20 of access instrument 10. As shown, pointed distal tip 57 of obturator 50 extends distally from distal end 16 of access instrument 10, while hub 55 of obturator 50 extends proximally from proximal end 14 of access instrument 10. More particularly, pointed distal tip 57 allows for penetration, or dissection through tissue. Flexible portion 59 of obturator 50 is deflected off axis or angulated relative to longitudinal axis "X" to conform to the curved configuration of curved portion 18 of shaft 12 of access instrument 10. However, due to the axial stiffness, or rigidity of flexible portion 59 of shaft 52, the shaft 52 is not compressed upon distal advancement of access instrument and obturator 10 and 50, respectively, through tissue. Accordingly, with obturator 50 positioned within access instrument 10, the access assembly may be advanced distally, lead by pointed distal tip 57 of obturator 50, through tissue to an internal surgical site. Obturator 50 may then be removed from access instrument 10 such that lumen 20 provides an access port, or cannula, for performing a minimally-invasive surgical procedure at the internal surgical site.

Figure 4A:
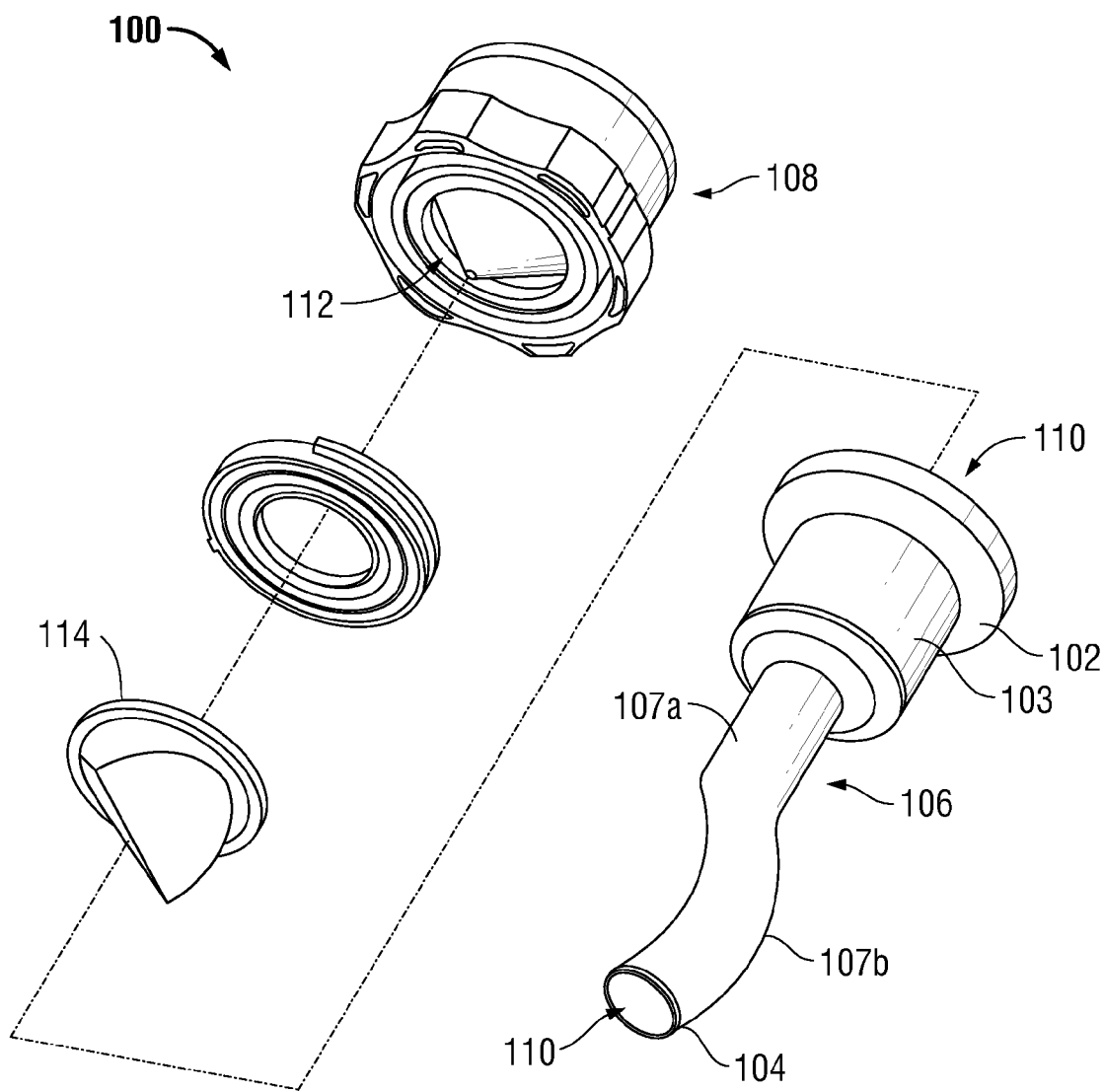
FIG. 4A is an exploded, perspective view of another embodiment of a pre-bent access instrument in accordance with the present disclosure.

Turning now to FIG. 4A, in one embodiment, trocar, or access instrument 100 includes respective proximal and distal ends 102, 104, a shaft or elongate member 106 disposed therebetween and seal housing 108. Access instrument 100 is similar to access instrument 10 discussed above.

Figure 4B:
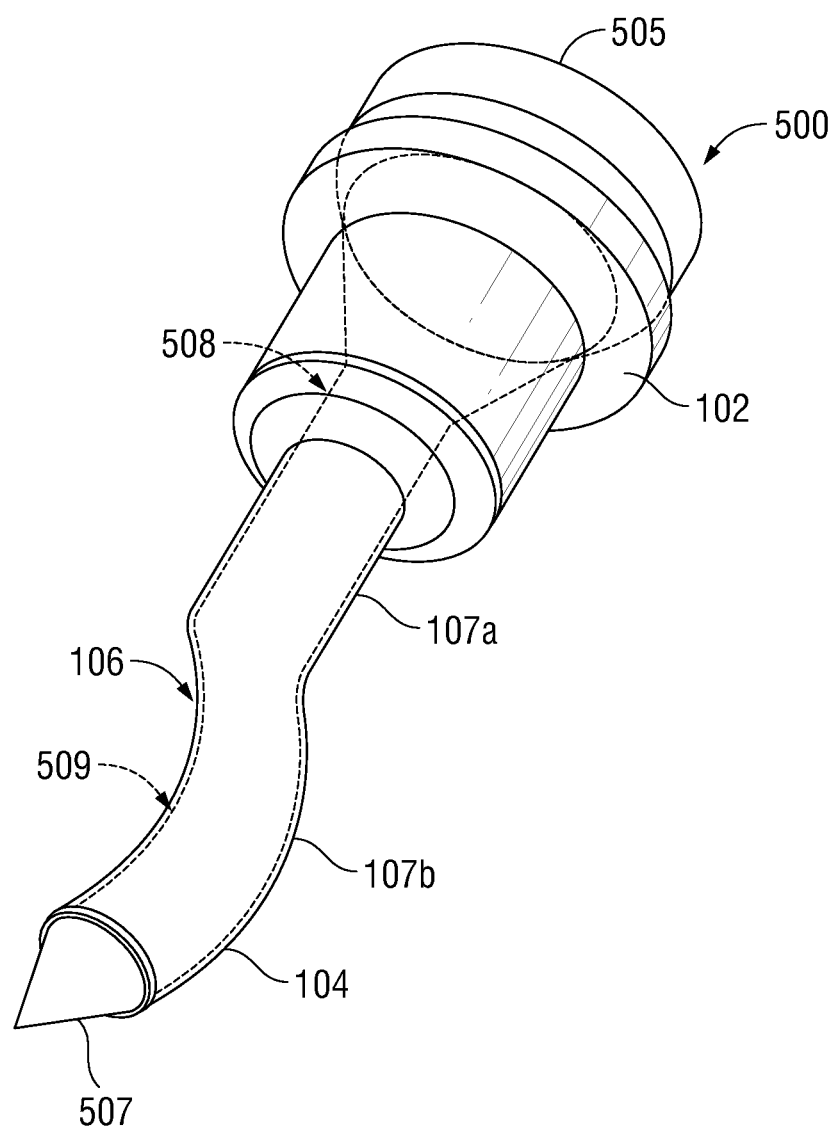
FIG. 4B is a perspective view of the pre-bent access instrument of FIG. 4A illustrating an obturator inserted therethrough.

Elongate member 106 of access instrument 100 includes a straight, or linear portion 107a and a curved, or bent portion 107b extending along at least a portion of the length thereof. Elongate member 106 further defines an opening 110 extending longitudinally therethrough that is dimensioned to permit the passage of surgical instrumentation therethrough, such as obturator 500 (FIG. 4B). As in the previous embodiment, obturator 500 includes a flexible portion 509 (FIG. 4B) configured to conform to curved portion 107b of access instrument 100 when inserted therethrough and a rigid portion 508 to provide structural support to obturator 500. Obturator 500 is similar to obturator 50 (FIG. 2).

Access instrument 100 includes seal housing 108 which is associated with or mounted to housing 103 of the access instrument 100. Seal housing 108 includes an instrument seal 112 that is adapted to receive surgical instrumentation inserted into longitudinal opening 110 so as to form a substantially fluid-tight seal therewith. Access instrument 100 may further includes a closure valve 114 within seal housing 108 or cannula housing 103 that is biased toward a closed position, but is adapted to open upon the introduction of the surgical instrumentation inserted into longitudinal opening 110 to allow the surgical instrumentation to pass therethrough. In the closed position, i.e., in the absence of surgical instrumentation, closure valve 114 creates a fluid-tight seal to, for example, inhibit insufflation gas for escaping through longitudinal opening 110 of access instrument 100.

Turning now to FIG. 4B, access instrument 100 is shown with obturator 500 inserted therethrough. More specifically, pointed distal tip 507 of obturator 500 extends distally from distal end 104 of access instrument 100, while hub 505 of obturator 500 extends proximally from proximal end 102 of access instrument 100. Further, flexible portion 507 of obturator 500 is bent, or conformed to pre-bent curved portion 107b of access instrument 100. From this position shown in FIG. 4B, the access assembly may be inserted through tissue or, as will be described below, may be inserted through an access portal, e.g., access portal 1000 (FIG. 5).

Figure 5:
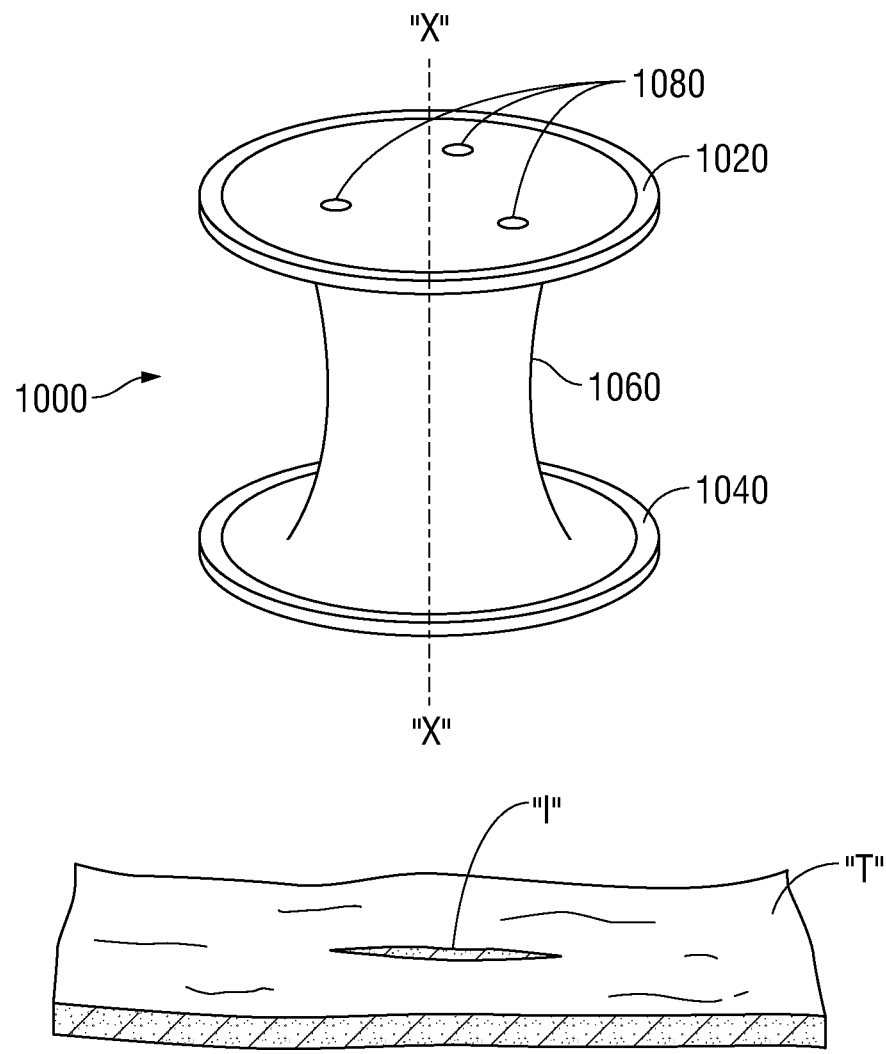
FIG. 5 is a side view of a compressible port anchor in accordance with the present disclosure configured for insertion into an incision in tissue.
Figure 6:
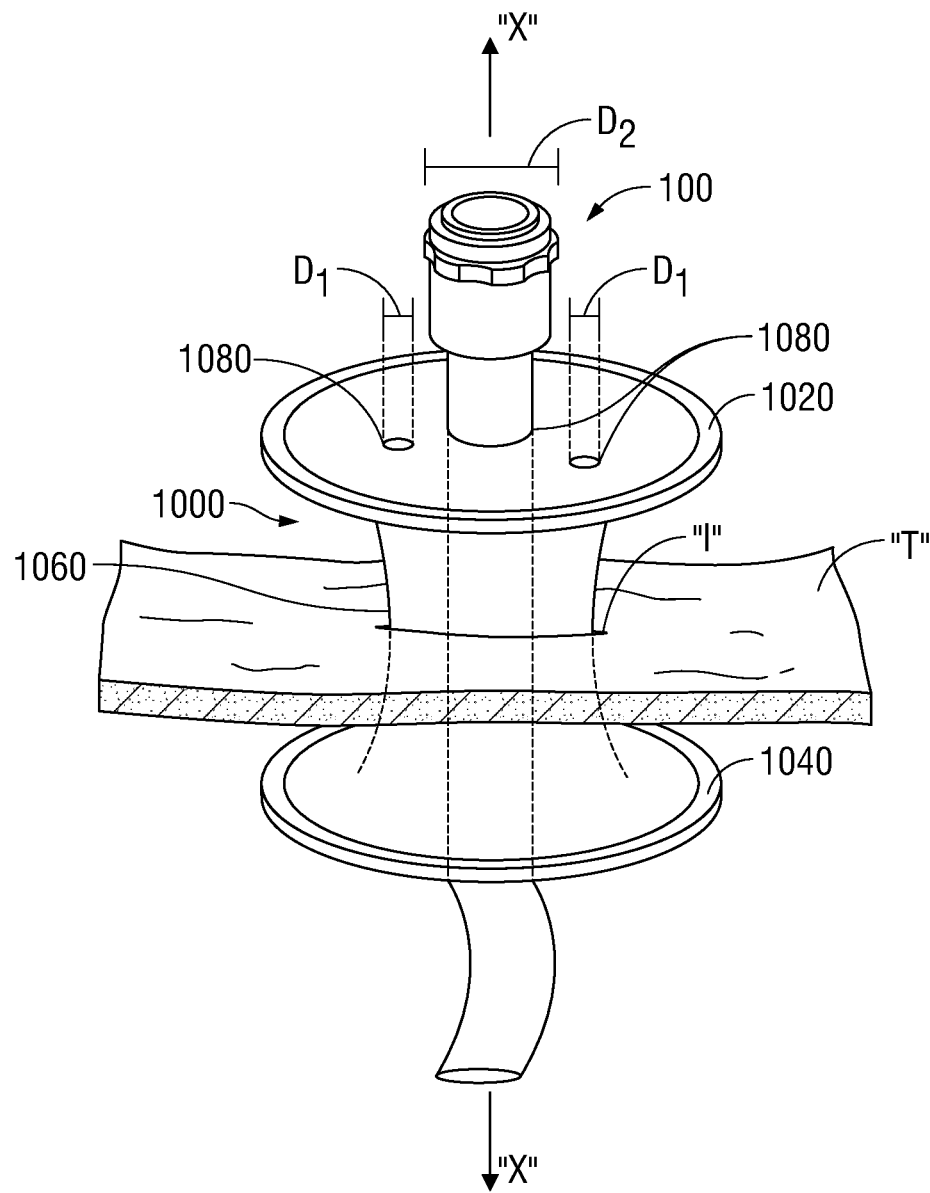
FIG. 6 is a side view of the compressible port anchor of FIG. 5 shown inserted through the incision in tissue and having a pre-bent access instrument inserted through a port thereof.

With reference now to FIGS. 5-6, a seal anchor member 1000 for use during a minimally-invasive surgical procedure is shown. Seal anchor member 1000 defines a longitudinal axis "X" and has a proximal end 1020, a distal end 1040, and an intermediate portion 1060 that is disposed between the proximal and distal ends 1020, 1040, respectively. Seal anchor member 1000 further includes one or more ports 1080 that extend longitudinally therethrough between proximal and distal ends 1020, 1040, respectively, thereof.

Seal anchor member 1000 may be formed from a suitable foam material, e.g., a polyisoprene foam, having sufficient compliance to form a seal about one or more surgical instruments, e.g., access instrument 100, inserted through one of ports 1080 and also to establish a sealing relation with surrounding tissue. It is envisioned that seal anchor member 1000 be sufficiently compliant to accommodate off axis motion of surgical instrumentation, e.g., access instrument 100, inserted therethrough. Seal anchor 1000 may be the port anchor disclosed in commonly assigned U.S. patent application Ser. No. 12/244,024, filed Oct. 2, 2008, the entire contents of such disclosure being incorporated herein.

As shown in FIGS. 5-6, proximal and distal ends 1020, 1040 of seal anchor member 1000 define substantially planar surfaces, although it is envisioned that either or both of proximal and distal ends 1020, 1040, respectively, of seal anchor member 1000 may define surfaces that are substantially arcuate to assist in the insertion of seal anchor member 1000 through an incision "I" in tissue "T."

Intermediate portion 1060 of seal anchor member 1000 extends longitudinally between proximal and distal ends 1020, 1040, respectively, of seal anchor member 1000. Intermediate portion 1006 varies in diameter along a length thereof. Accordingly, seal anchor member 1000 defines a cross-sectional dimension that varies along a length thereof to facilitate the anchoring of seal anchor member 1000 within an incision in tissue. In one embodiment, seal anchor member 1000 defines an "hour-glass" shape or configuration to assist in anchoring seal anchor member 1000 within an incision in tissue. In cross-section, intermediate portion 1060 may exhibit any suitable configuration, e.g., substantially circular, oval or oblong.

Each port 108 extending through anchor seal member 1000 is configured to removably receive a surgical instrument (e.g., access instrument 10) therethrough. Prior to the insertion of surgical instrumentation, each of ports 1080 is disposed in a first state wherein each of ports 1080 defines a first or initial dimension $D_1$ (FIG. 6). Initial dimension $D_1$ (FIG. 6) may be about 0 mm such that the escape of insufflation gas (not shown) through ports 1080 of seal anchor member 1000 in the absence of a surgical instrument inserted therethrough is substantially inhibited. For example, each port 1080 may be configured as a slit extending longitudinal through seal anchor member 1000. Upon the introduction of surgical instrumentation through one (or more) of ports 1080, port 1080 transitions to a second state in which port 1080 defines a second, larger dimension $D_2$ (FIG. 6) that substantially approximates the diameter of the surgical instrument disposed therethrough such that a substantially fluid-tight seal is formed therearound and such that the escape of insufflation gas (not shown) through port 1080 of seal anchor member 1000 is substantially inhibited.

The use and function of access instrument 100 in conjunction with seal anchor member 1000 will be discussed during the course of a typical minimally invasive procedure with reference to FIGS. 4A-7. However, it is envisioned that the cannula assembly, i.e., access instrument 100 and obturator 500, may be configured for use independently of seal anchor member 1000 and/or in conjunction with any other suitable seal member (not shown).

Initially, the peritoneal cavity (not shown) is insufflated with a suitable biocompatible gas, e.g., $CO_2$ gas, such that the cavity wall is raised and lifted away from the internal organs and tissue housed therein, providing greater access thereto. The insufflation may be performed with an insufflation needle or similar device, as is conventional in the art. Either prior or subsequent to insufflation, an incision "I" is created in tissue "T", the dimensions of which may be varied dependent upon the nature of the procedure.

Prior to the insertion of seal anchor member 1000 within the incision in tissue, seal anchor member 1000 is in its expanded condition in which the dimensions thereof inhibit the insertion of seal anchor member 1000 into the incision "I" in tissue "T." To facilitate insertion, the clinician transitions seal anchor member 1000 into the compressed condition by applying a force thereto, e.g., by squeezing seal anchor member 1000. This applied force acts to reduce the radial dimensions of the proximal and distal ends 1020, 1040, respectively, of anchor seal member 1000 and similarly reduces the radial dimension of intermediate portion 1060 such that seal anchor member 1000 may be inserted into the incision "I" in tissue "T." Subsequent to insertion, distal end 1040 of seal anchor member 1000 is positioned beneath tissue "T" at which time seal anchor member 1000 may be allowed to transition from the compressed condition back to the expanded condition by removing the force thereon.

During the transition from the compressed condition to the expanded condition, the dimensions of seal anchor member 1000 are increased such that intermediate portion 1060 creates an internal biasing force that is directed outwardly and exerted upon surrounding tissue, thereby creating a substantially fluid-tight seal between the seal anchor member 1000 and surrounding tissue, while proximal and distal ends 1020, 1040, respectively, extend radially from the incision "I" in tissue "T" on the respective external and internal surfaces thereof. Thus, once in position, seal anchor member seals, or inhibits the escape of insufflation gas from the internal surgical site.

Once seal anchor member 1000 is positioned within the incision "I" in tissue "T," as described above, one or more surgical instruments may be inserted through ports 1080. Surgical instrumentation introduced through one of ports 1080 may be any suitable surgical instrument and, accordingly, may vary in size. Suitable surgical instruments may include graspers, forceps, clip-appliers, staplers, etc. Other access instruments such as, for example, access instrument 100, may also be introduced through seal anchor member 1000 such that additional surgical instrumentation may be inserted through access instrument 100 (once obturator 500 has been removed from lumen 110 of access instrument 100) and advanced to the surgical site.

More specifically, with obturator 500 inserted trough access instrument 100, as shown in FIG. 4B, the access assembly may be inserted, lead by pointed distal tip 507 of obturator 500, through one of ports 1080, enlarging port 1080 and thereby transitioning port 1080 into the second state in which port 1080 defines a second dimension $D_2$ that substantially approximates the diameter of access instrument 100, creating a substantially fluid tight seal about access instrument 100 and inhibiting the escape of insufflation gas (not shown) through port 1080 of seal anchor member 1000, as discussed above. Access instrument 100 may then be advanced into position adjacent the internal surgical site.

Figure 7:
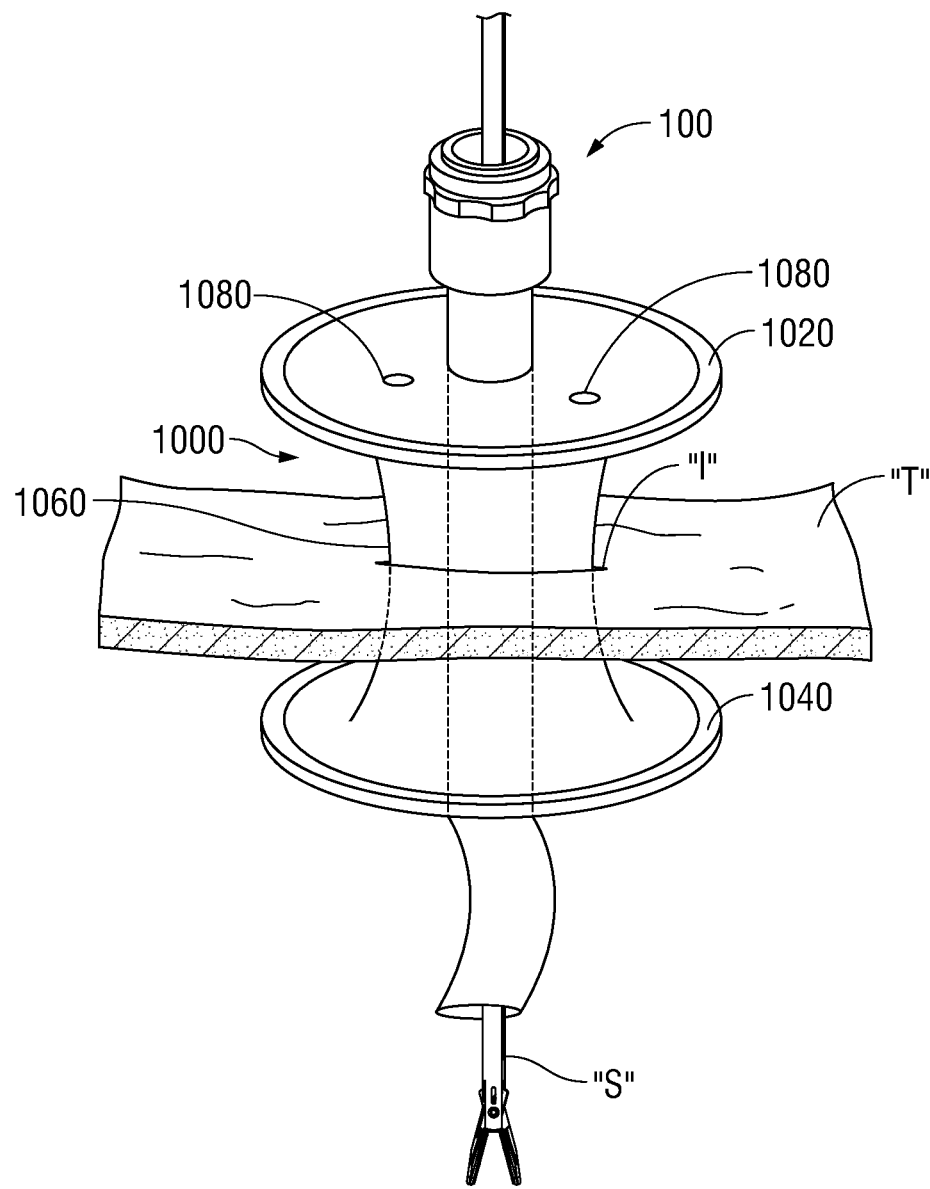
FIG. 7 is a side view of the compressible port anchor of FIG. 5 shown inserted through the incision in tissue with a pre-bent access instrument inserted through a port thereof and a flexible surgical grasper inserted through the pre-bent access instrument.

With reference now to FIG. 7, once access instrument 100 is disposed through access portal 1000, as shown in FIG. 6, and is positioned as desired for the particular minimally-invasive surgical procedure to be performed at the internal surgical site, obturator 500 may be removed from access instrument 100. As such, other surgical instrumentation, e.g., surgical grasper "S," may be inserted through opening 110 of access instrument 100 to perform a minimally-invasive surgical procedure at the internal surgical site. One surgical instrument contemplated will have a flexible section adapted to conform or follow the pre-bent or curved configuration of access instrument 10. Such instruments with flexible shafts are disclosed in commonly assigned U.S. Pat. Nos. 4,473,077 and 7,546,993 and U.S. Patent Publication No. 2009/0090765, the entire contents of each disclosure being incorporated herein. As mentioned above, instrument seal 112 maintains a fluid-tight seal about surgical grasper "S" when inserted through access instrument 100. Additionally, the pre-bent, or curved configuration of access instrument 100 helps prevent interference, tangling, or "chop-sticking" of surgical instrumentation inserted through the various ports 1080 of seal anchor member 1000, particularly where multiple surgical instruments are inserted through seal anchor member 1000 and/or where multiple seal ports, e.g., seal anchor members 1000, are used.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A cannula assembly, comprising:
    a cannula including:
        a housing having a seal dimensioned to establish a seal about an object introduced therethrough; and
        an elongated shaft dimensioned to access tissue, the elongated shaft having a lumen extending therethrough, the elongated shaft defining a longitudinal axis and having proximal and distal ends, the elongated shaft including a first shaft segment having a first pre-determined configuration and a second shaft segment distal of the first shaft segment, the second shaft segment being rigid and having a second pre-determined configuration different from the first pre-determined configuration; and
    an obturator including:
        an elongated body adapted for insertion through the lumen of the elongated shaft, the elongated body having proximal and distal ends and including a first body segment having a configuration in general accordance with the first pre-determined configuration of the first shaft segment and a flexible second body segment selectively adaptable to conform to the second pre-determined configuration of the second shaft segment upon insertion through the lumen of the elongated shaft.

2. The cannula assembly according to claim 1, wherein the first pre-determined configuration of the first shaft segment defines a general linear segment and the first body segment of the elongated body defines a general corresponding linear segment.

3. The cannula assembly according to claim 1, wherein the second pre-determined configuration of the second shaft segment defines a general arcuate segment, whereby, upon insertion of the elongated body through the lumen of the elongated shaft, the second body portion of the elongated body is positioned in the second pre-determined configuration having a general corresponding arcuate segment.

4. The cannula assembly according to claim 1, wherein the second shaft segment of the elongated shaft is disposed adjacent the distal end of the elongated shaft.

5. The cannula assembly according to claim 1, wherein the second shaft segment of the elongated shaft is disposed intermediate the proximal and distal ends of the elongated shaft.

6. The cannula assembly according to claim 1, wherein the distal end of the elongated body defines a conical-shaped configuration to facilitate advancement through tissue.

7. The cannula assembly according to claim 1, wherein the elongated body defines a longitudinal axis, the second body segment of the elongated body initially positioned in general alignment with the longitudinal axis of the elongated body, whereby, upon insertion of the elongated body through the lumen of the elongated shaft, the second body segment is positioned in general oblique relation with the longitudinal axis in general accordance with the second pre-determined configuration of the second shaft segment.

8. The cannula assembly according to claim 1, wherein the flexible second body segment of the elongated body is formed from a spring coil.

9. The cannula assembly according to claim 1, wherein the lumen of the elongated shaft defines a proximal entry opening at the proximal end of the elongated shaft and a distal exit opening at the distal end of the elongated shaft, at least portions of the proximal entry opening and the distal exit opening in longitudinal alignment with each other relative to the longitudinal axis.

10. The cannula assembly according to claim 1, wherein the first body segment of the elongated body of the obturator is rigid.

11. The surgical access assembly according to claim 1, wherein the flexible second body segment of the elongated obturator body is formed from a spring coil.

12. A surgical access system, comprising:
   an anchor member positionable within a passage in tissue, the anchor member comprising a compressible material and defining a proximal end, a distal end and an intermediate portion, the anchor member adapted to transition between an at least partially compressed condition to facilitate introduction within the passage in tissue and an at least partially expanded condition to substantially anchor the anchor member relative to the tissue, the anchor member including at least one port extending therethrough; and
   a cannula assembly including a cannula defining a longitudinal axis and a lumen extending therethrough, the cannula positionable within the at least one port of the anchor member whereby inner surfaces defining the at least one port establish a seal about the cannula, the cannula including a cannula segment offset with respect to the longitudinal axis.

13. The surgical access assembly according to claim 12 including an obturator including an elongated obturator body adapted for insertion through the lumen of the cannula, the obturator body having a flexible body segment adapted to follow the path defined by the offset cannula segment, the elongated body having an end dimensioned to extend beyond the cannula and configured to facilitate advancement of the obturator and cannula through the at least one port of the anchor member.

14. The surgical access assembly according to claim 13, wherein the offset cannula segment defines a general arcuate segment, whereby, upon insertion of the obturator body through the lumen of the cannula, the flexible body segment of the obturator body is positioned within the offset cannula segment having a general corresponding arcuate segment.

15. The surgical access assembly according to claim 12, further including a surgical instrument having an elongated shaft with a flexible shaft segment and an end effector adapted to perform a surgical task, the surgical instrument being dimensioned for advancement through the lumen of the cannula in the absence of the obturator whereby the flexible shaft segment follows the path defined by the offset cannula segment.

16. The surgical access assembly according to claim 15, wherein the cannula includes a seal, the seal dimensioned to establish a seal about the shaft of the surgical instrument.

17. The surgical access assembly according to claim 16, wherein the lumen of the cannula defines a proximal entry opening at a proximal end of the cannula and a distal exit opening at a distal end of the cannula, at least portions of the proximal entry opening and the distal exit opening in longitudinal alignment with each other relative to the longitudinal axis.

* * * * *